US012785974B2

(12) United States Patent
Blanco

(10) Patent No.: US 12,785,974 B2
(45) Date of Patent: Nov. 3, 2026

(54) SYSTEM AND ANALYSIS METHOD FOR THE IDENTIFICATION OF HUMAN BIOLOGICAL MATERIAL

(71) Applicant: Stefani Blanco, Buenos Aires (AR)

(72) Inventor: Stefani Blanco, Buenos Aires (AR)

( * ) Notice: Subject to any disclaimer, the term of this patent is extended or adjusted under 35 U.S.C. 154(b) by 0 days.

(21) Appl. No.: 18/779,428

(22) Filed: Jul. 22, 2024

(65) Prior Publication Data

US 2025/0323792 A1 Oct. 16, 2025

(30) Foreign Application Priority Data

Apr. 16, 2024 (AR) ............................ P20240100960

(51) Int. Cl.
*H04L 9/32* (2006.01)
*C12Q 1/6844* (2018.01)
*C12Q 1/6869* (2018.01)
*G01N 27/447* (2006.01)
*G16B 50/30* (2019.01)
*G16B 50/40* (2019.01)

(52) U.S. Cl.
CPC .......... *H04L 9/3231* (2013.01); *C12Q 1/6844* (2013.01); *C12Q 1/6869* (2013.01); *G01N 27/447* (2013.01); *G16B 50/30* (2019.02); *G16B 50/40* (2019.02)

(58) Field of Classification Search
CPC ....... H04L 9/3231; G16B 50/40; G16B 50/30; C12Q 1/6869; C12Q 1/6844; G01N 27/447
See application file for complete search history.

(56) References Cited

U.S. PATENT DOCUMENTS 8,261,094 B2 * 9/2012 King ..................... G06F 21/606 713/168
9,704,154 B2 * 7/2017 Xing ................... G10L 21/0208
(Continued)

FOREIGN PATENT DOCUMENTS

KR 20230126220 A * 8/2023 ........... C12Q 1/6876

OTHER PUBLICATIONS

Mark Barash., Ayeleth Reshef, Paul Brauner; "The Use of Adhesive Tape for Recovery of DNA from Crime Scene Items"; "https://onlinelibrary.wiley.com/doi/10.1111/j.1556-4029.2010.01416.x"; Jul. 1, 201; pp. 1-16.*

*Primary Examiner* — Mohammad A Siddiqi
(74) *Attorney, Agent, or Firm* — Defillo & Associates, Inc.; Evelyn A. Defillo

(57) ABSTRACT

A system and analysis procedure for identifying human biological material," which includes a fingerprint reader device that captures the biometric data of the fingerprints from the subject under analysis, verifying the identity of each sample. It incorporates artificial intelligence (AI) that not only performs pattern recognition but also generates a unique identification parameter for each analysis. Additionally, the system encrypts the data to protect the identity of each study. The procedure involves collecting a sample of epithelial cells from the hands of the subject under analysis using an adhesive film device. The collected samples are processed using a DNA extraction and purification kit to conduct the sequencing of the DNA sample and generate a DNA profile. This process converts the characteristics of human genetic material into a DNA sequence.

3 Claims, 12 Drawing Sheets

(56) References Cited

U.S. PATENT DOCUMENTS

| | | | | |
|---|---|---|---|---|
| 2016/0012465 | A1* | 1/2016 | Sharp | G06Q 20/321 705/14.17 |
| 2020/0296093 | A1* | 9/2020 | Hoyos | H04L 9/3247 |
| 2021/0174426 | A1* | 6/2021 | Isaacson | G06Q 20/12 |
| 2021/0272125 | A1* | 9/2021 | Kopf | H04L 9/50 |
| 2024/0331579 | A1* | 10/2024 | Ambartsoumian | G09F 3/0288 |
| 2025/0246099 | A1* | 7/2025 | Ambartsoumian | B65C 3/20 |
| 2025/0278075 | A1* | 9/2025 | Wu | G05B 19/41865 |

* cited by examiner

SYSTEM AND ANALYSIS METHOD FOR THE IDENTIFICATION OF HUMAN BIOLOGICAL MATERIAL

1. TECHNICAL FIELD OF THE INVENTION

This application relates to a "system and method for analysis for the identification of biological material from individuals," which involves identifying DNA (deoxyribonucleic acid) from persons and analyzing an individual's DNA to determine their unique identity.

DNA analysis involves extracting a biological sample, such as blood, saliva (epithelial cells), sweat, hair, or tissue, followed by using a technique such as PCR (Polymerase Chain Reaction) or restriction fragment electrophoresis to amplify and analyze specific regions of the DNA. The analyzed regions typically consist of short repetitive sequences known as microsatellites or single nucleotide polymorphisms (SNPs).

Once the analysis is conducted, DNA profiles are compared with other known DNA profiles or genetic databases to identify matches or determine genetic relationships.

The analysis of genetic markers is known as "short tandem repeats."

It is important to emphasize that the collection, use, and disclosure of DNA profiles must comply with standards regarding the protection of personal data.

The term "personal data" is used to refer to any information related to an identified or identifiable individual.

Several devices and methods have been developed for genetic identification and determination of parentage of individuals for forensic use, using DNA obtained from blood samples or swabs containing epithelial cells from the mouth, tissue samples, or bone material.

2. BACKGROUND OF THE INVENTION AND PROBLEMS TO BE SOLVED

One of the fundamental principles of forensic analysis is the use of procedures that ensure that the collected evidence is protected through a secure and traceable chain of custody. The samples must be identified using a system that uniquely and indisputably individualizes each sample. The assignment of sample codes must be unique and centralized in a single database to prevent duplications. It is essential to maintain traceability of the original codes, especially in cases where these may need to be modified throughout the process.

The prior art recognizes the existence of various types of stickers or films consisting of at least two layers of biaxially oriented polypropylene of different thicknesses, linked with different types of adhesives, and composed of different compounds or bases. These stickers or films allow for revealing and identifying a person's fingerprints and/or collecting genetic material (DNA samples) in various quantities.

Known issues in DNA collection through blood extraction.

Known issues in DNA collection through blood extraction consider the use of anticoagulants, which are contraindicated for patients awaiting organ transplants or who have undergone transplants, as well as those with coagulation disorders such as cancer (CA), leukemia, hemophilia, idiopathic thrombocytopenic purpura (ITP), lymphomas, among others. In conditions with cerebellar disorders that cause involuntary or uncontrollable movements such as tremors, stiffness, difficulty with balance and coordination, and/or in patients with mental disorders such as ataxia, schizophrenia, phobias (OCD), Parkinson's disease, Huntington's disease, or in specific patient groups such as children, applying traditional blood extraction methods becomes challenging. This is also the case for individuals with Tourette syndrome, cerebral pathologies, or middle ear disorders, among others.

Known challenges in DNA collection through buccal swabs.

Various commercial devices enable the non-invasive collection of epithelial cells from the buccal mucosa through swabs (typically 2-3 swabs). These kits or equipment are specifically designed for the collection of such samples.

In addition to the issues mentioned in the previous paragraph, known challenges in DNA collection through buccal swabs include difficulties in reading the sample if the individual has eaten before collection and if the individual has smoked. Another challenge is the potential contamination of the sample by oral bacteria. Moreover, alterations in readings have been detected related to the administration of antibiotics. Samples of DNA collected through buccal swabs cannot be stored under normal environmental conditions because saliva contains bacteria that proliferate rapidly in humidity. Warm and humid environments are particularly destructive to DNA, and high temperatures lead to DNA sample degradation. While the procedure is not painful, the process of rubbing the inside of the cheek with the swab can be uncomfortable for some people.

It has been demonstrated that up to 70% of errors in a forensic laboratory originate from contamination, incorrect preservation, improper identification, or mishandling during the safeguarding and transportation of the sample.

3. PROPOSED SOLUTION

The contribution of the "system and method for analysis for the identification of biological material from individuals" includes a non-invasive adhesive film device for collecting DNA samples and a sample storage device linked with a QR identification code to ensure traceability. This QR code is associated with a digital fingerprint ID of the individual from whom the sample is taken, encrypted using a symmetric key algorithm to validate fingerprint recognition against the obtained genetic fingerprint. The system also includes means to store this information in a relational database.

The DNA sample collection and genetic study procedure is simple, non-invasive, and includes a conservation and custody device with securely encrypted data for traceability and sample tracking.

In the prior art, various types of sample collection devices for genetic analysis exist, including adhesives with different compounds or bases that allow for the adherence of epithelial cells (DNA samples) in varying quantities.

The genetic information of an individual is contained in the sequence of bases of a DNA strand, which consists of the ordered arrangement of the nucleotides A (adenine), G (guanine), T (thymine), and C (cytosine). This base sequence can be considered a coded language, where each combination of nucleotides forms a specific message in the DNA.

During DNA transcription to RNA and subsequent translation to proteins, nucleotides are grouped into triplets called codons, where each codon encodes a specific amino acid.

Some codons act as start signals or termination signals during genetic translation.

There are 64 possible codons because there are four nucleotides, and each codon is composed of 3 nucleotides.

However, since there are only 20 amino acids, some are encoded by more than one codon, making the genetic code redundant.

Thus, the result obtained from sequencing a DNA sample returns an encrypted code based on four letters (A, G, T, and C), specific for bioinformatics, using file formats such as "FASTA" and "FASTQ":

The most widely used system for analyzing a DNA profile is the Combined DNA Index System (CODIS), which is requested by most countries. Prior to accessing the CODIS system, an agreement must be entered into with the U.S. Federal Bureau of Investigation (FBI).

In the case of a biometric fingerprint (subject's fingerprint), there are international encoding standards such as the ANSI/NIST-ITL (ANSI/NIST) Standard Information Technology and the MD5 format, which is a Message-Digest Algorithm 5. These standards define standard formats for interoperability of biometric data, including fingerprints. Fingerprints are often encoded in hexadecimal strings, a cryptographic hash algorithm widely used to verify that a file has not been modified. The common program used for identifying and verifying individuals through their fingerprints is the Automated Fingerprint Identification System (AFIS).

The validation of biometric fingerprint recognition against the genetic fingerprint obtained from the DNA sample includes using an artificial intelligence algorithm. This algorithm encompasses methods not only for pattern recognition but also for providing an identification parameter to compare and evaluate the similarity between both biometric characteristics.

The preferred collection device consists of a "film," which includes multiple layers of overlaid polypropylene sheets biaxially oriented, bonded together, and associated with an acrylate adhesive layer, specifically designed for use in forensic medicine.

The film described above is associated with a known and commercially used method for extracting, analyzing, and typing samples. It is also linked to a device designed for secure sample protection and storage, featuring a georeferenced QR code fingerprint identification on each device to locate its position.

Additionally, to validate the sample, an encrypted fingerprint (biometric fingerprint) of the fingerprint of the individual whose sample is collected is included. Thus, the DNA sample is validated by comparing the fingerprint and digital biometric data obtained from the individual whose epithelial cell samples were collected.

The genetic fingerprint and biometric fingerprint information are encrypted to ensure confidentiality using AES (Advanced Encryption Standard) symmetric key encryption. This encryption is associated with a QR code on the NEO-M8N location device, enabling the determination of the sample's location and traceability as needed by the user's search demand.

Storage Device

It comprises a capsule closed on its three lateral sides, with a single longitudinal opening and a lid to insert the film containing the collected DNA sample. It is made of high-density polyethylene (HDPE) or (PEAD), which is a non-toxic synthetic polymer resistant to impacts and chemicals, with high-temperature resistance between 130° C. and 140° C. The device includes, on its upper side, a laser-printed identification code of the 'QR' type with a geolocation device for the location and traceability of the sample upon user request.

The procedure comprises the following stages:

Analysis procedure for the identification of biological material from individuals, used according to the system of claim 1, characterized by comprising the following stages:

i. A fingerprint reader device (1) is used to capture the fingerprint image of the individual from whom the sample was collected.

ii. Processing the captured fingerprint image using a processing unit (9) to extract biometric data from the individual whose sample is being analyzed, generating a unique data profile for biometric fingerprint identification (Hd).

iii. An adhesive film device (2) is used to collect DNA samples from the hands of the individual whose sample is being collected.

iv. Process the collected sample using the commercial kit (3).

v. Amplify the collected sample of human genetic material (DNA) using a thermocycler, conduct electrophoresis and sequencing of the DNA sample, and generate a DNA profile using a generator (8), converting the characteristics of the human genetic material into a DNA sequence.

vi. Process the DNA sequence of the individual whose sample is being analyzed using a processing unit (10) and encrypt the data through an encryption module (4) to create a DNA profile (Hg) generating a unique data identification profile (ID).

vii. An AI algorithm verifies the correspondence and validity between the biometric fingerprint (Hd) and the DNA profile (Hg) information.

viii. Encrypt the biometric fingerprint data (Hd) and DNA profile (Hg) using an encryption module (3) and an AI algorithm, generating a unique data identification profile (ID).

ix. Safeguard the DNA sample in a storage device (6) with a QR code for identification.

x. Enter the identification profile (ID) along with the QR code identification of the storage device (6) into a database unit (7).

4. DESCRIPTION OF THE FIGURES

For greater clarity and understanding of the object of the present invention, it has been illustrated in the following figures. It is depicted in one of the preferred embodiments, allowing users and experts in the field to envision many additional variations. To facilitate understanding of the constructive, constitutive, and functional characteristics, a preferred embodiment example is described below, schematically depicted in the accompanying sheets, without a specific scale. This does not imply limitations to the scope of protection of the present invention application, as it is an example. It does not assign an exclusive character to the scope of protection of the present invention but merely serves an explanatory and illustrative purpose of its underlying concept, where:

FIG. **5*a*** illustrates the test conducted showcasing the procedure, values, and results obtained.

Figure 1:
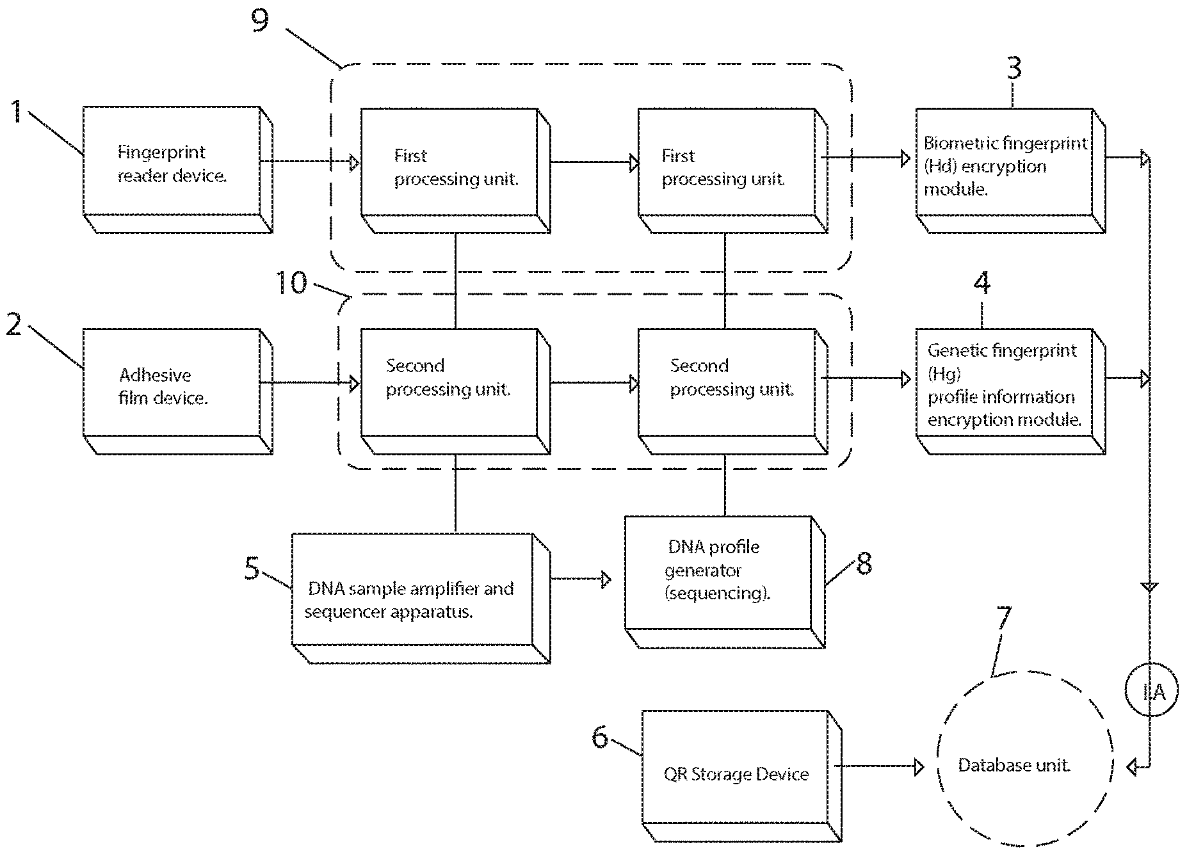
FIG. 1 illustrates a schematic diagram of the components involved in the invention's system.
Figure 2:
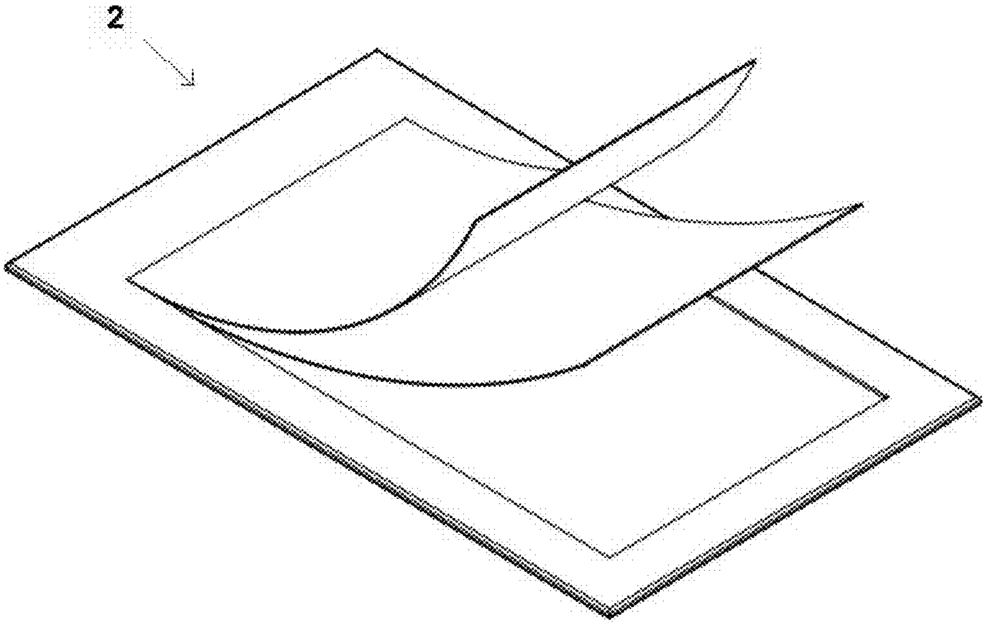
FIG. 2 illustrates a top-perspective view of the adhesive film device.
Figure 3:
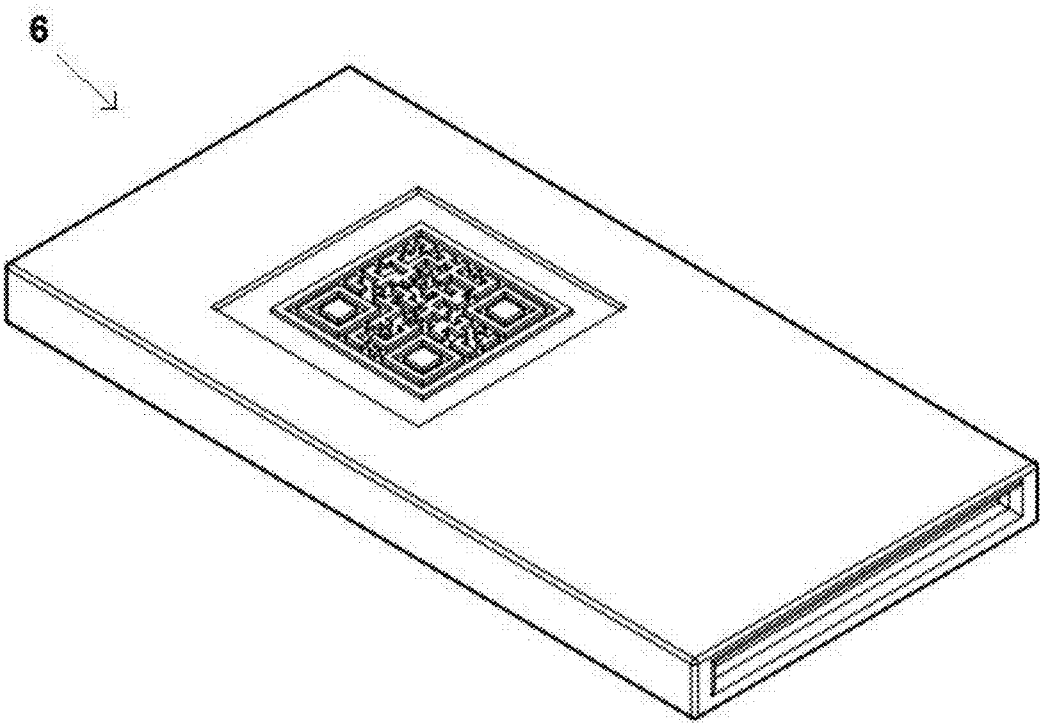
FIG. 3 illustrates a top-right perspective view of the storage device with a QR code on its upper surface.
Figure 4:
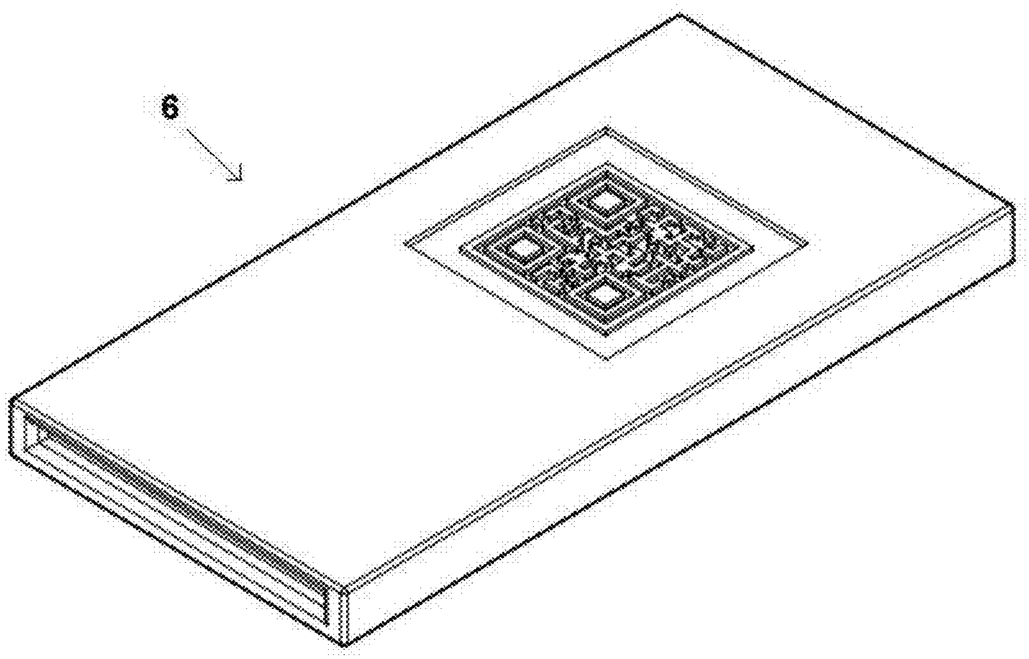
FIG. 4 illustrates a top left perspective view showing the storage device with a QR code on its upper surface.
Figure 5A:
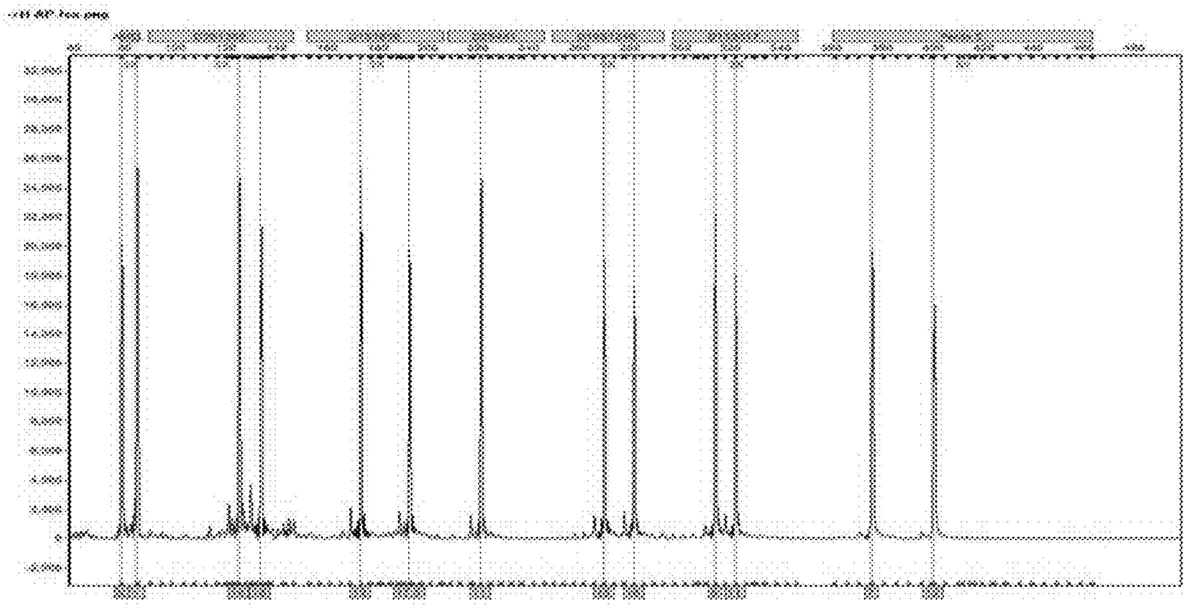
Figure 5B:
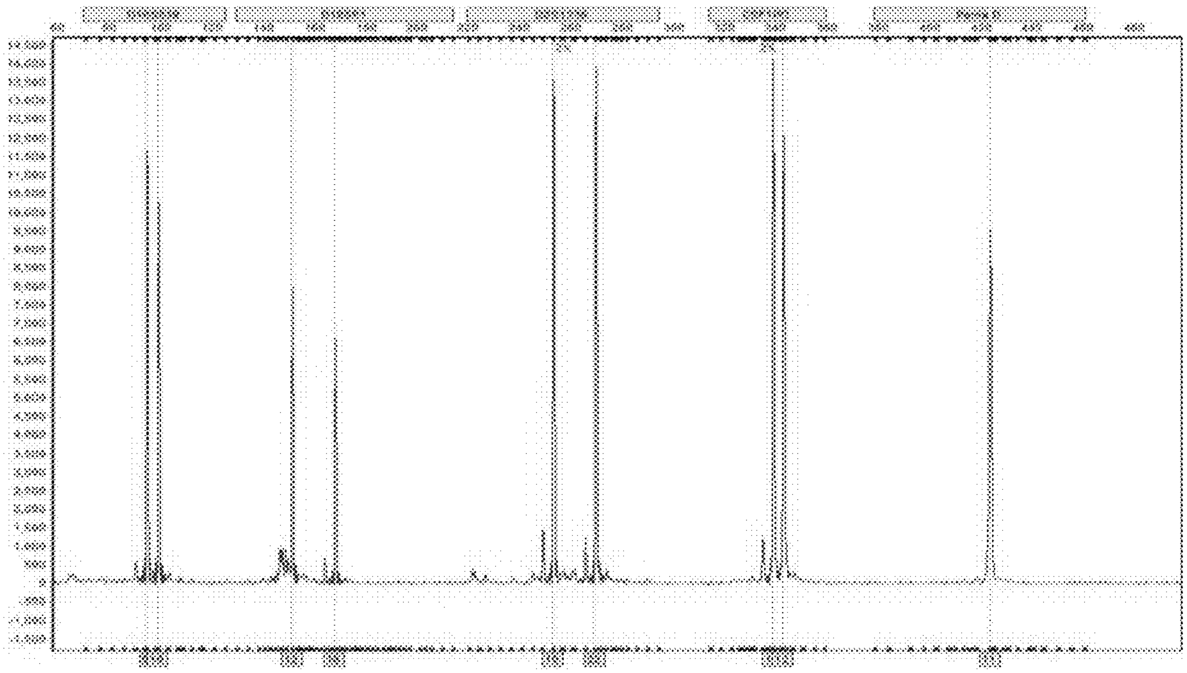

FIG. 5*b* illustrates another test conducted showcasing the illustrates the tests conducted showcasing the procedure, values, and results obtained.

Figure 5C:
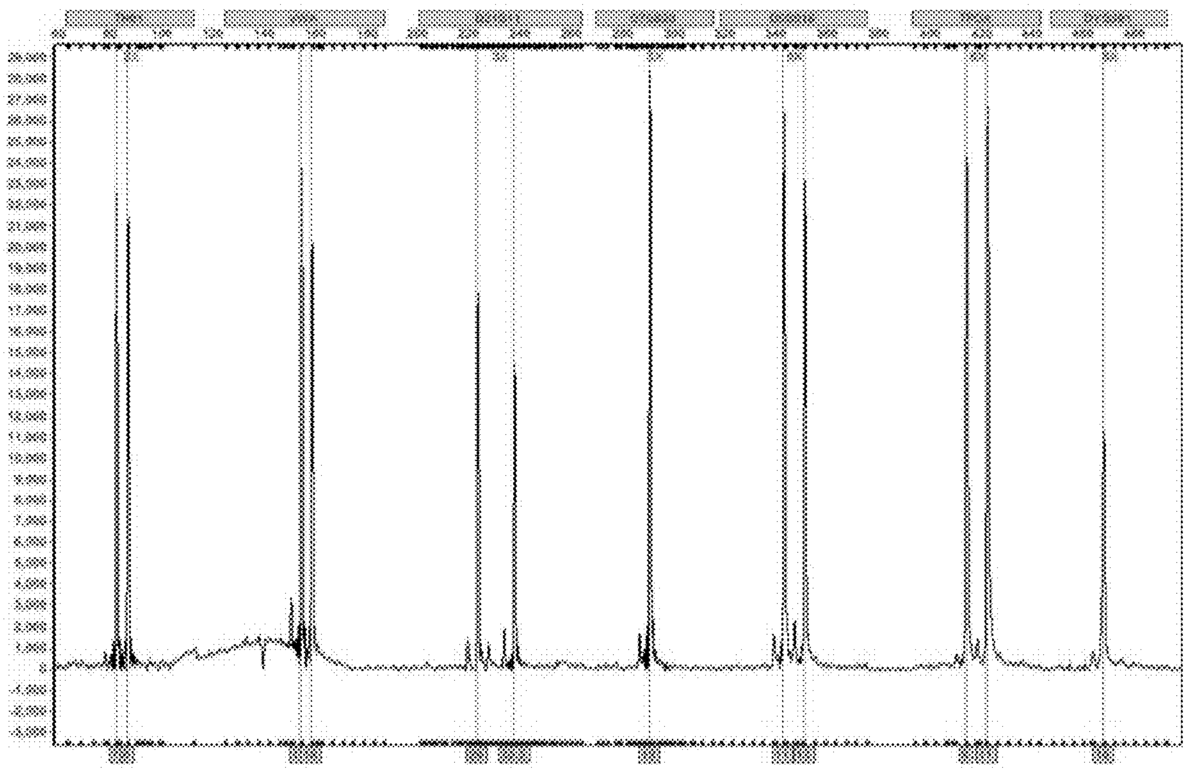

FIG. 5*c* illustrates another test conducted showcasing the illustrates the tests conducted showcasing the procedure, values, and results obtained.

Figure 5D:
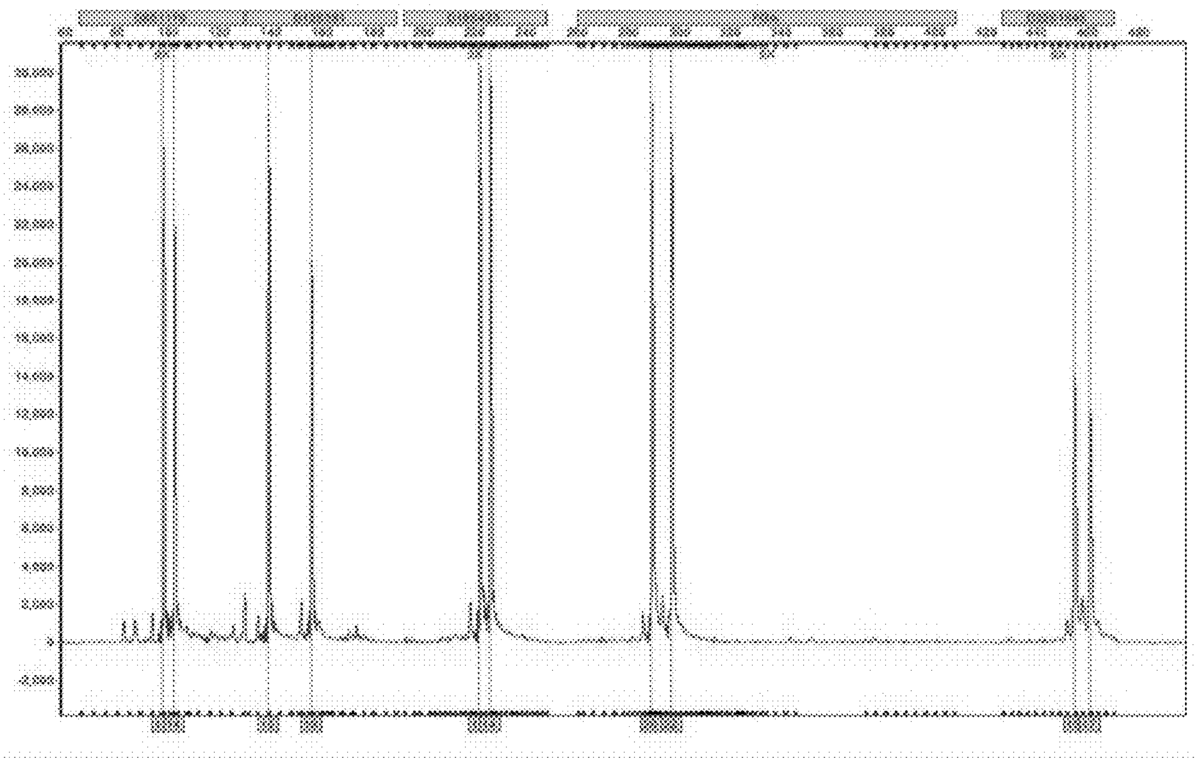

FIG. 5*d* illustrates another test conducted showcasing the illustrates the tests conducted showcasing the procedure, values, and results obtained.

Figure 6A:
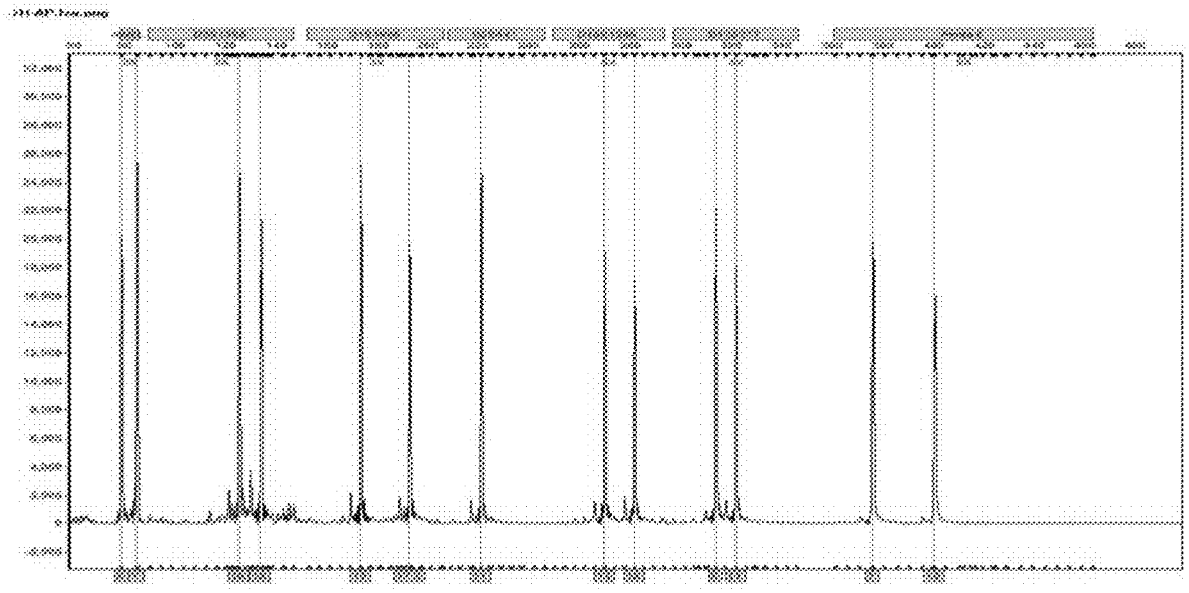

FIG. 6*a* illustrates another test conducted showcasing the illustrates the tests conducted showcasing the procedure, values, and results obtained.

Figure 6B:
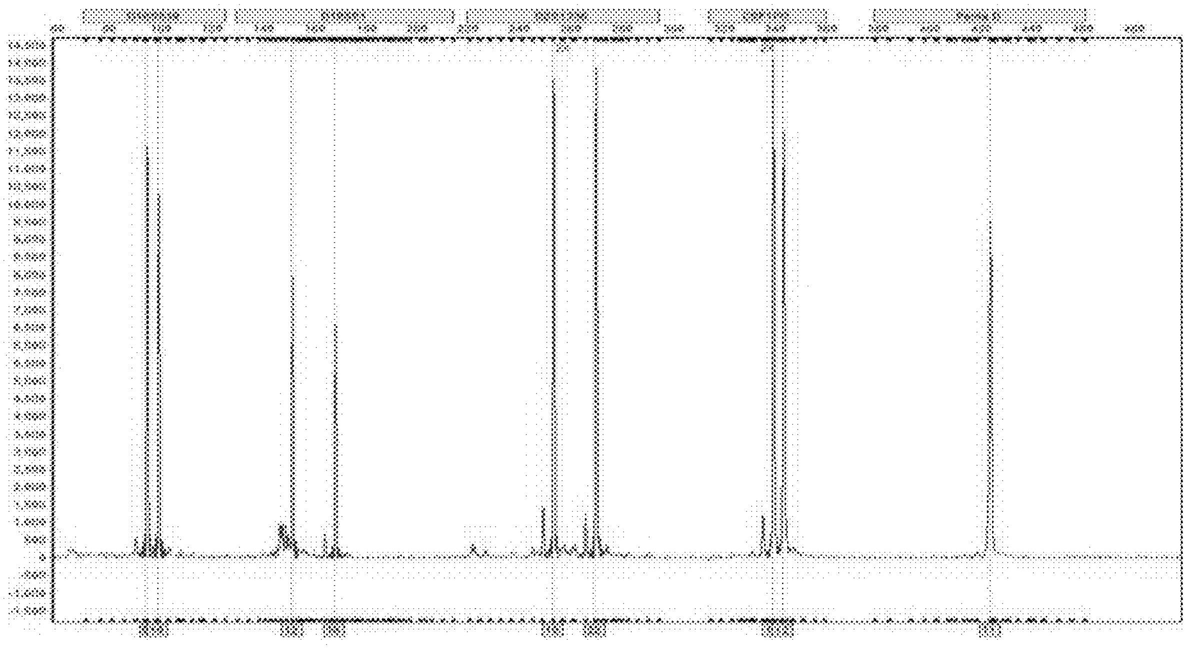

FIG. 6*b* illustrates another test conducted showcasing the illustrates the tests conducted showcasing the procedure, values, and results obtained.

Figure 6C:
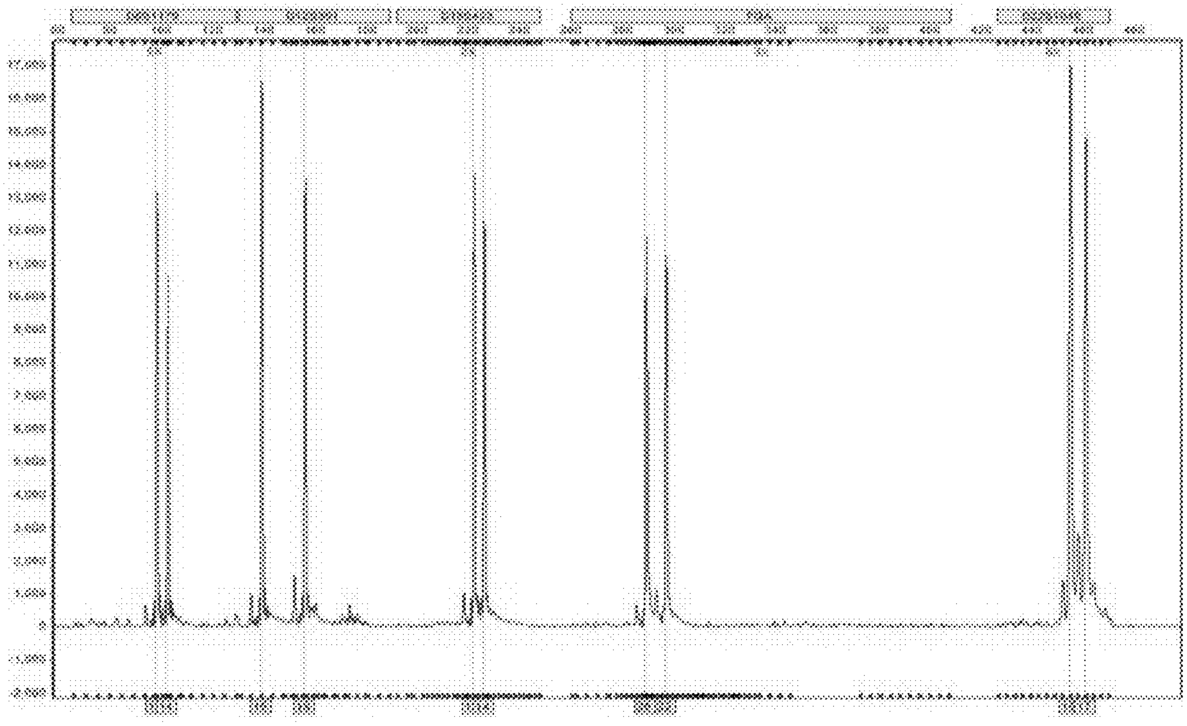

FIG. 6*c* illustrates another test conducted showcasing the illustrates the tests conducted showcasing the procedure, values, and results obtained.

Figure 6D:
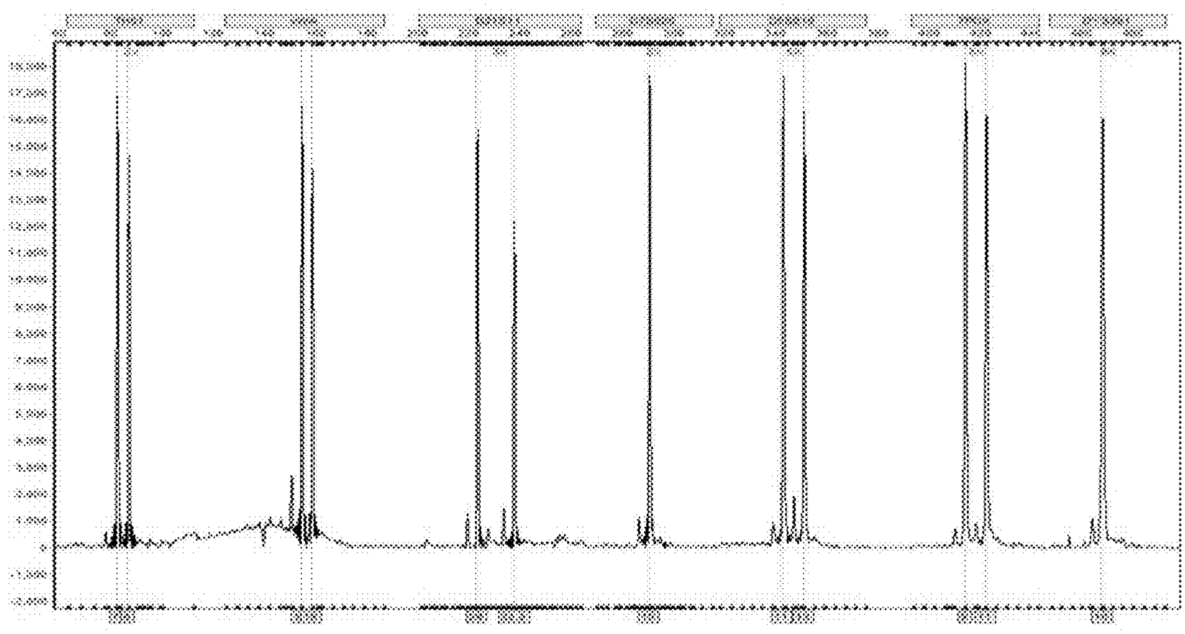

FIG. 6*d* illustrates another test conducted showcasing the illustrates the tests conducted showcasing the procedure, values, and results obtained.

5. DETAILED DESCRIPTION OF THE INVENTION

The components involved in the invention's system are the following:

1. Fingerprint reader device.
2. Adhesive film device.
3. Biometric fingerprint (Hd) encryption module.
4. Genetic fingerprint (Hg) profile information encryption module.
5. DNA sample amplifier and sequencer apparatus.
6. QR Storage Device
7. Database unit.
8. DNA profile generator (sequencing).
9. First processing unit.
10. Second processing unit.

The objective proposed in the present application involves an adhesive film collection device associated with a non-invasive procedure that allows for sufficient quantity and adequate quality extraction of genetic material (DNA). This aims to obtain a genetic fingerprint suitable for identification and forensic comparison in DNA databases without altering the conditions of the sample during extraction and storage. It includes encryption algorithms to safeguard the security of encrypted data and maintain traceability of the original codes for each stored reserved sample in a storage device (8) with a digital identification code (QR) for the genetic material sample. This is designed to surpass the prior art in the field.

The system comprises a fingerprint reader device to capture the biometric data of the fingerprints from the subject under analysis, verifying the identity of each sample. It includes artificial intelligence (AI) that incorporates capabilities for pattern recognition and provides a unique identification parameter for each analysis. Additionally, the system encrypts the data to protect the identity of each study.

The procedure involves collecting a sample of epithelial cells from the hands of the subject under analysis using an adhesive film device. The collected samples are processed using a DNA extraction and purification kit to conduct the sequencing of the DNA sample and generate a DNA profile. This process converts the characteristics of human genetic material into a DNA sequence.

With the necessary tools for the procedure: a thermocycler, a sequencer, and an electrophoresis process.

To verify the correspondence and validity of the biometric fingerprint (Hd) with the genetic fingerprint (Hg) DNA profile, an artificial intelligence (AI) validation algorithm is included. This algorithm contains capabilities for pattern recognition and provides an identification parameter through an algorithm.

Once the identification is validated, the genetic fingerprint (Hg) and biometric fingerprint (Hd) information will be encrypted, generating a unique data identification profile (ID) for each sample.

To safeguard the DNA sample for any future requirements, it is placed in a storage device with a QR code identification. This allows the entry of the identification profile (ID) into the database, the QR code identification of the storage device, and its physical location. This protects the identity of the subject under analysis, which can only be accessed through access keys.

The input data consists of two sets of biometric features:

The fingerprint characteristics (digital fingerprint) are represented as Hd, Hd.

The characteristics obtained from the genetic fingerprint are represented as Hg, Hg.

To assess the similarity by calculating a similarity measure between the two sets;

$$D(Hd, Hg)\backslash = \sum i\backslash = 1\, n(hd,\, i - hg,\, i)2$$

Where Hd Hd are the feature vectors of the fingerprint, and Hg Hg are the feature vectors of the genetic fingerprint, respectively.

Furthermore, hd, ihd,i, and hg,i are the individual features in the sets of characteristics Hd Hd and Hg Hg, respectively.

Where n is the number of features in each set.

Where Hd Hd are the feature vectors of the fingerprint, and Hg Hg are the feature vectors of the genetic fingerprint, respectively.

Once the distance between the fingerprint and genetic fingerprint characteristics is calculated, a decision threshold can be established to determine whether both samples originate from the same individual. For example, if the calculated distance is less than a predefined threshold, the samples can be considered to originate from the same individual; otherwise, they would be regarded as samples from different individuals. Cross-validation tests are performed to optimize the evaluation of the system's accuracy.

Tests Performed

According to FIGS. 5 and 6, the following tests were conducted to demonstrate and characterize the device's and method's behavior.

Example Embodiment

Technical report on genetic fingerprints obtained by collecting epithelial cells from hands using adhesive film, compared with genetic fingerprint obtained from a buccal swab sample. Of equal quality without altering the sample conditions during the collection and storage process.

Objective

This study evaluated the adhesive film's ability to collect epithelial cells from the hands, specifically the palms and fingers. The aim was to obtain biological material suitable for DNA analysis, enabling studies for human identification purposes. While the previous technique can be performed on any individual, it specifically focuses on populations who cannot undergo invasive sampling due to various circumstances.

Description of the Test

The analysis aimed to establish that sufficient human biological material, specifically obtained from epithelial cells collected from an individual's hands, can be extracted to get adequate human genetic material (DNA). This material can be quantified, amplified, and typed to establish a genetic fingerprint suitable for analysis, thereby enabling the identification of a specific individual. This procedure was validated by obtaining the same human genetic material but collected from a buccal swab sample, demonstrating consistency between both methods.

The biological material used for comparing both methods, i.e., the samples taken from the hands and the buccal swabs, was collected from four randomly selected individuals from the population, who voluntarily agreed to have their samples taken for the study.

The hand samples collected using adhesive film and the buccal swab samples collected using a sterile swab were subjected to genetic material (DNA) extraction using a manual extraction technique with the commercial Qiagen kit. Subsequently, the quantity of genetic material each sample contained was determined through quantification.

The human genetic material from each sample (hands and buccal swabs from each individual) was amplified using PCR for the twenty-three markers contained in the commercial PowerPlex Fusion kit (Promega Corp) and typed by capillary electrophoresis using the Genetic Analyzer ABI 3500.

The genetic profiles obtained from buccal swab samples and those obtained from the samples collected using adhesive film for the four tested individuals are detailed in the SoftGenetics GeneMarker HID v2.9.5 report tables, establishing correspondence between both sets of results.

The tables show the results of genetic fingerprints from buccal swab samples, in this case, labeled as H-AP, H-El, H-JP, and H-SB, versus the results of genetic fingerprints from samples taken from the palms and hands using adhesive film from the same individuals, in this case, labeled as GS-AP, GS-El, GS-JP, and GS-SB.

The graphs presented following the report correspond to the electropherogram obtained for each sample (signals in different colors indicating the type of fluorophore used) performed by capillary electrophoresis. This technique allows the separation of DNA molecules at different speeds as they migrate according to their charge in an electrophoretic field. These signals show the DNA sequence of each individual. With the specific analysis software (GeneMarker HID V2.95), it is possible to transform these signals into the number of repeats in a given sequence, thus obtaining the genetic fingerprint of a specific sample.

The graphical representation of the DNA fragments identified for each individual was obtained using the PCR (polymerase chain reaction) technique with the PowerPlex Fusion kit (Promega Corp), which utilizes twenty-two autosomal genetic markers. The genetic markers AMEL and DYS391 are not included within the twenty-two identifiers, as they indicate sex and lineage, respectively.

It is noted that the human genetic material (DNA) obtained using the adhesive film technique is of sufficient quantity and quality to produce a valuable genetic fingerprint for identification and comparison.

This technique is supported by the following test data under the following conditions as technical support:

The adhesive film's ability to extract DNA of sufficient quality for human identification studies via capillary electrophoresis was evaluated.

Samples were collected from 4 male individuals using buccal swabs and adhesive film.

Technical personnel wearing appropriate personal protective equipment (apron, gloves, and mask) collected the samples. Buccal swabs were initially taken using sterile cotton swabs. Each cotton swab was separated from its wooden shaft using a sterile scalpel and placed into a sterile 1.5 ml Eppendorf tube previously labeled.

Each individual was asked to press their palms and fingers firmly onto the adhesive, which were immediately covered with the protective film to capture cellular material on the adhesive film. A sterile cotton swab was lightly soaked with the extraction buffer from the commercial kit to extract cellular material from the adhesive film. The cellular material was then collected by swabbing the adhesive film and transferred into sterile Eppendorf tubes for subsequent DNA extraction. DNA extraction from all samples was performed using the Qiagen commercial kit. Subsequently, amplification of the 23 markers included in the PowerPlex Fusion commercial kit (Promega Corp) was conducted, followed by typing via capillary electrophoresis using the Genetic Analyzer ABI 3500 equipment.

SoftGenetics (see FIG. 5*a, b, c, d*)

GeneMarker HID V2.9.5 Allele Report

Project Comments:

Sample 1: Ref Ladder: LADDER-1.fsa Run date and time: 08/25/2023-6:54:10 PM→08/25/2023-7:22:55 PM Dye: Blue, Green, Yellow, Red—0 peaks Sample 2: Ref Ladder: LADDER-1.fsa Run date and time: 08/25/2023-6:54:10 PM→08/25/2023-7:22:55 PM Dye: Blue, Green, Yellow, Red—0 peaks Sample 3: Ref Ladder: LADDER-1.fsa Run date and time: 08/25/2023-6:54:10 PM→08/25/2023-7:22:55 PM Dye: Blue, Green, Yellow, Red—0 peaks Sample 4: Ref Ladder: LADDER-1.fsa Run date and time: 08/25/2023-6:54:10 PM→08/25/2023-7:22:55 PM Dye: Blue, Green, Yellow, Red—0 peaks

| BUCCAL SWABS | AMEL | D3S1358 | D1S1656 | D2S441 | D10S1248 | D13S317 | Penta E | D16S539 | D18S51 |
|---|---|---|---|---|---|---|---|---|---|
| H-AP | X, Y | 16, 16 | 13, 17.3 | 11 | 13, 16 | 9, 11 | 7, 12 | 9, 10 | 12, 16 |
| H-EI | X, Y | 14, 17 | 15, 16.3 | 14 | 15 | 9, 11 | 5, 20 | 8, 10 | 13, 14 |
| H-JP | X, Y | 17, 18 | 13, 15 | 11 | 14, 16 | 11, 12 | 7 | 9 | 16, 17 |
| H-SB | X, Y | 15, 18 | 16, 18.3 | 10, 11 | 14, 17 | 11, 12 | 10, 13 | 11 | 12, 17 |

-continued

| | D2S1338 | CSF1PO | Penta D | TH01 | vWA | D21S11 | D7S820 | D5S818 | TPOX |
|---|---|---|---|---|---|---|---|---|---|
| H-AP | 18, 22 | 11, 12 | 11 | 7, 8 | 17, 18 | 29, 22.2 | 10 | 11, 13 | 9, 11 |
| H-EI | 17, 18 | 10, 11 | 9, 11 | 6, 9 | 14, 17 | 31, 33.2 | 8, 10 | 10, 13 | 8, 12 |
| H-JP | 22, 23 | 11, 12 | 11 | 7 | 17 | 29, 31 | 9, 10 | 7, 11 | 11 |
| H-SB | 20 | 11, 13 | 9, 13 | 7, 9.3 | 14, 17 | 30 | 10, 12 | 11, 13 | 9, 11 |

| | DYS391 | D8S1179 | D12S391 | D19S433 | FGA | D22S1045 |
|---|---|---|---|---|---|---|
| H-AP | 10 | 13, 14 | 15, 19 | 13, 14 | 20, 22 | 15, 17 |
| H-EI | 10 | 13, 16 | 21, 26 | 12, 13 | 23, 26 | 15, 16 |
| H-JP | 10 | 13, 14 | 15, 20 | 13, 14 | 20, 23 | 15, 17 |
| H-SB | 11 | 11, 12 | 16, 21 | 12, 15 | 23, 25 | 15 |

Project Comments: (See FIG. 6*a, b, c, d*)

Sample 1: Ref Ladder: LADDER-1.fsa Run date and time: 08/25/2023-6:21:22 PM→08/25/2023-6:52:13 PM Dye: Blue, Green, Yellow, Red—0 peaks Sample 2: Ref Ladder: LADDER-1.fsa Run date and time: 08/25/2023-6:21:22 PM→08/25/2023-6:52:13 PM Dye: Blue, Green, Yellow, Red—0 peaks Sample 2: Ref Ladder: LADDER-1.fsa Run date and time: 08/25/2023-6:21:22 PM→08/25/2023-6:52:13 PM Dye: Blue, Green, Yellow, Red—0 peak

| SB | AMEL | D3S1358 | D1S1656 | D2S441 | D10S1248 | D13S317 | Penta E | D16S539 | D18S51 |
|---|---|---|---|---|---|---|---|---|---|
| GS-AP | X, Y | 16, 18 | 13, 17.3 | 11 | 13, 16 | 9, 11 | 7, 12 | 9, 10 | 12, 16 |
| GS-EI | X, Y | 14, 17 | 15, 16.3 | 14 | 15 | 9, 11 | 5, 20 | 6, 10 | 13, 14 |
| GS-JP | X, Y | 17, 18 | 13, 15 | 11 | 14, 16 | 11, 12 | 7 | 9 | 16, 17 |
| GS-SB | X, Y | 15, 18 | 16, 18.3 | 10, 11 | 14, 17 | 11, 12 | 10, 13 | 11 | 12, 17 |

| | D2S1338 | CSF1PO | Penta D | TH01 | vWA | D21S11 | D7S820 | D5S818 | TPOX |
|---|---|---|---|---|---|---|---|---|---|
| GS-AP | 18, 22 | 11, 12 | 11 | 7, 8 | 17, 18 | 29, 32.2 | 10 | 11, 13 | 9, 11 |
| GS-EI | 17, 18 | 10, 11 | 9, 11 | 6, 9 | 14, 17 | 31, 33.2 | 8, 10 | 10, 13 | 8, 12 |
| GS-JP | 22, 23 | 11, 12 | 11 | 7 | 17 | 29, 31 | 9, 10 | 7, 11 | 11 |
| GS-SB | 20 | 11, 13 | 9, 13 | 7, 9.3 | 14, 17 | 30 | 10, 12 | 11, 13 | 9, 11 |

| | DYS391 | D8S1179 | D12S391 | D19S433 | FGA | D22S1045 |
|---|---|---|---|---|---|---|
| GS-AP | 10 | 13, 14 | 15, 19 | 13, 14 | 20, 22 | 15, 17 |
| GS-EI | 10 | 13, 16 | 21, 26 | 12, 13 | 23, 26 | 15, 16 |
| GS-JP | 10 | 13, 14 | 15, 20 | 13, 14 | 20, 23 | 15, 17 |
| GS-SB | 11 | 11, 12 | 16, 21 | 12, 15 | 23, 25 | 15 |

Results Obtained

The results'analysis confirmed that the genetic profile obtained using the adhesive film technique on hands and fingers coincides with that obtained from a buccal swab sample from the same individual.

The system and analysis procedure for identifying human biological material described and exemplified herein are encompassed within the scope of protection of the present patent application, as outlined primarily by the following claim clauses.

The invention claimed is:

1. An analysis system for identifying a human biological material, which involves the identification of an individuals by DNA (deoxyribonucleic acid), the system analyzes the DNA of at the individual to determine an unique identity, the analysis system comprising:

- a fingerprint reader device (1) for capturing a biometric data from fingerprints of the individual to verify sample identity;
- an artificial intelligence capable of pattern recognition and providing a unique identification parameter for each analysis; wherein the captured data is encrypted using a biometric fingerprint encryption module (3) to protect the identity of each study;
- an adhesive film device (2) for collecting epithelial cell samples from the hands of the individual; the adhesive film device (2) including an adhesive film having multiple layers of polypropylene sheet biaxially oriented and bonded together and an acrylate layer, wherein after the identity verification (ID), the data is linked to a genetic fingerprint (Hg) encryption module (4) for DNA profile information; an amplifier and DNA sequencer apparatus (5) associated with a DNA profile generator (8);
- a storage device (6) to safeguard DNA samples, the storage device (6) includes a QR code and an opening to insert the adhesive film containing the DNA sample;
- a database unit (7) for storing identity verification (ID),
- wherein the QR code is associated with a digital fingerprint identification (ID) of the individual, the QR code is encrypted with an algorithm to validate the fingerprint recognition.

2. An analysis procedure for the identification of biological material from individuals using the system of claim 1, the procedure comprising the following steps:

- using a fingerprint reader device (1) to capture the fingerprint image of the individual from whom the sample was collected;
- processing the captured fingerprint image using a processing unit (9) to extract biometric data from the individual whose sample is being analyzed, generating a unique biometric fingerprint identification profile (Hd) of data;
- using an adhesive film device (2) to collect DNA samples from the hands of the individual whose sample is being collected;
- amplifying the collected sample of human genetic material (DNA) using a thermocycler, conduct electrophoresis and sequencing of the DNA sample, and generate a DNA profile using a generator (8), converting the characteristics of the human genetic material into a DNA sequence;
- using a processing unit (10) to process the collected sample from the individual under examination for the DNA profile (Hg), generating a unique data identification profile (ID);
- verifying the correspondence and validity between the biometric fingerprint (Hd) and the DNA profile (Hg) information using an AI algorithm;
- encrypting the biometric fingerprint data (Hd) and DNA profile (Hg) using an encryption module (3) and an AI algorithm, generating a unique data identification profile (ID);
- safeguarding the DNA sample in a storage device (6) with a QR code for identification; and
- entering the identification profile (ID) along with the QR code identification of the storage device (6) into a database unit (7).

3. The analysis system according to claim 1, wherein the storage device includes a laser-printed identification code and a geolocation device.

* * * * *